United States Patent [19]

Sanderson

[11] Patent Number: 5,391,378
[45] Date of Patent: Feb. 21, 1995

[54] TWO-PART MEDICINAL TABLET AND METHOD OF MANUFACTURE

[75] Inventor: Richard Sanderson, McKeesport, Pa.

[73] Assignee: Elizabeth-Hata International, Inc., North Huntingdon, Pa.

[21] Appl. No.: 20,611

[22] Filed: Feb. 22, 1993

[51] Int. Cl.$^6$ ............................ A61K 9/20; A61K 9/24
[52] U.S. Cl. .................................... 424/464; 424/467; 424/468; 424/473; 424/474
[58] Field of Search ............... 424/464, 467, 473, 468; 425/406; D24/100, 101, 102, 103

[56] References Cited

U.S. PATENT DOCUMENTS

| | | | |
|---|---|---|---|
| 4,803,076 | 2/1989 | Ranade | 424/438 |
| 4,816,262 | 3/1989 | McMullen | 424/467 |
| 4,824,677 | 4/1989 | Shah et al. | 424/467 |
| 4,842,867 | 6/1989 | Ayer et al. | 424/473 |

Primary Examiner—Thurman K. Page
Assistant Examiner—James M. Spear
Attorney, Agent, or Firm—Buchanan Ingersoll; George Raynovich, Jr.

[57] ABSTRACT

A medicinal tablet mechanical configuration is provided that permits prolonged absorption of a medicinal dosage through the gastro-intestinal tract of warm blooded animals. The tablet is formed with a solid core unit that contains the medically beneficial drug and an outer unit that maintains its physical and chemical integrity during the dosage life of the core unit. The medicinal tablet is formed in a die by first placing a quantity of powder from which the outer unit is formed into the die. The core unit is next positioned within the die so that portions of the surface of the core unit abut the die. The remainder of the powder to form the outer unit is then placed in the die and the contents of the die are subjected to a compressive force by die punches inserted into the die so that the tablet is formed. At the points where the core unit abuts the die, the core unit is exposed through the outer unit so that the drug in the core unit is released slowly rather than the entire surface of the core unit being exposed which would cause more rapid absorption of the drug in the intestinal tract.

16 Claims, 2 Drawing Sheets

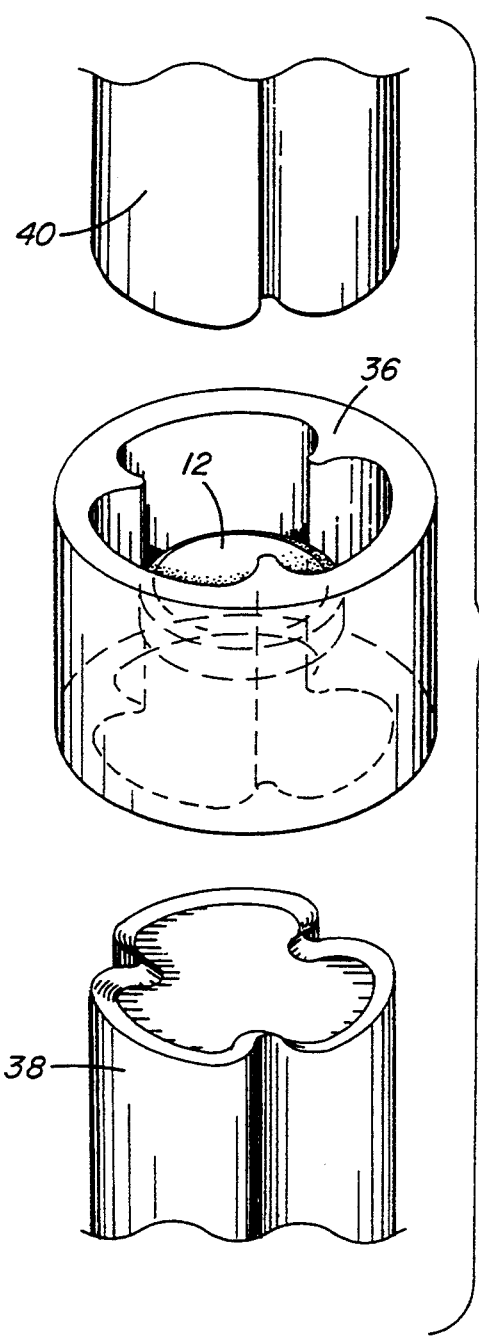
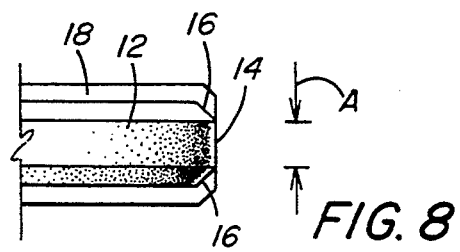
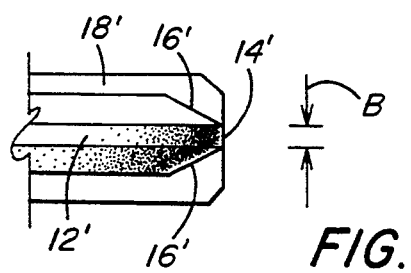

TWO-PART MEDICINAL TABLET AND METHOD OF MANUFACTURE

BACKGROUND OF THE INVENTION

1. Field of the Invention

This invention relates to a two-part medicinal tablet in which an outer unit surrounds a core unit containing a medically beneficial drug. The outer unit is constructed to permit a small portion of the core unit to be exposed through the outer unit. The invention includes the method of forming the two-part medicinal tablet in the die of a tablet making machine.

2. Description of the Prior Art

In providing medically beneficial drugs to warm blooded animals, it is often useful to prolong the absorption of the drug into the blood stream of the animal through the gastro-intestinal tract. Various methods have been proposed for prolonging the absorption of medically beneficial drugs so that the drugs function over a longer period of time after a medicinal tablet is swallowed by a warm blooded animal. In this context, the term "warm blooded animal" includes warm blooded mammals, humans, primates, household pets, farm animals and any other warm blooded member of the animal kingdom.

Various ways of prolonging the absorption of medically beneficial drugs through the gastro-intestinal tract of warm blooded animals have been proposed. As an example, U.S. Pat. No. 4,842,867 describes an elaborate dosage form to provide for prolonged assimilation of a beneficial drug into the blood stream of warm blooded animals through the gastro-intestinal tract. The elaborate arrangement of parts disclosed in that patent makes the dosage form relatively expensive to manufacture.

The present invention is directed to providing a two-part medicinal tablet which can be readily manufactured in a modified tableting machine that is used for high speed production throughout the pharmaceutical industry. The two-part medicinal tablet of the present invention provides prolonged absorption of a medically beneficial drug by warm blooded animals.

SUMMARY OF THE INVENTION

In accordance with the present invention, there is provided a medicinal tablet having a solid core unit formed from a medically beneficial drug. An outer unit, surrounding the core unit, is formed by pressing a powdered material into the shape of the outer unit that surrounds the core unit. The outer unit is of a shape that it exposes a preselected amount of the surface area of the core unit through the outer unit when the outer unit is formed around the core unit.

Further, in accordance with the present invention, a method of forming, in a die, a medicinal tablet having a solid core unit surrounded by an outer unit with a preselected amount of surface area of the core unit being exposed through the outer unit is provided. A solid core unit having the desired medically beneficial drug and shaped as a generally cylindrical flat tablet is obtained. A quantity of powder from which the outer unit is formed is inserted into a die having the peripheral shape of the outer unit. The solid core unit is inserted into the die so that portions of the core unit cylindrical surface abut the die and the die locates the core unit at a fixed lateral position within the die. A second quantity of powder from which the outer unit is formed is inserted into the die over the core unit. A mating punch is inserted into the die and sufficient compressive force is exerted on the die and the mating die punch to form the first and second quantities of powder into the shape of the outer unit whereby the core unit is exposed through the outer unit at those places on the core unit cylindrical surface that abut the die. The tablet is then removed from the die.

Accordingly, an object of the present invention is to provide an improved two-part medicinal tablet which prolongs the absorption of a medically beneficial drug through the gastrointestinal tract of warm blooded animals.

Another object of the present invention is to provide a two-part medicinal tablet which may be readily manufactured in a modified tablet forming machine that is widely utilized in the pharmaceutical industry.

Another object of the present invention is to provide a method for manufacturing an improved two-part medicinal tablet of the type described.

These and other objects of the present invention will be more completely disclosed as this description proceeds in conjunction with the accompanying drawings and appended claims.

BRIEF DESCRIPTION OF THE DRAWINGS

FIG. 7 is an expanded view of the die and upper and lower punches of a tablet making machine utilized to form the medicinal tablet of FIGS. 1–5, inclusive.

FIG. 8 is an elevation showing a core unit of the present invention having a specified cylindrical height.

FIG. 9 is an elevation similar to FIG. 8 showing the core unit having a reduced cylindrical height.

DESCRIPTION OF THE PREFERRED EMBODIMENT

Figure 1:
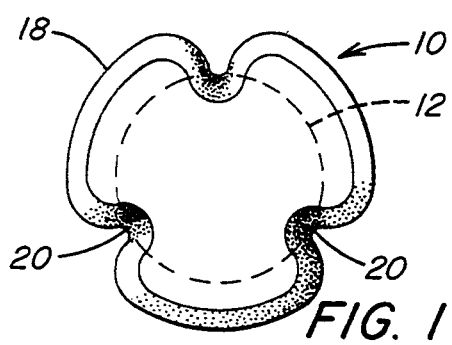
FIG. 1 is a top plan view of the medicinal tablet of the present invention.
Figure 2:
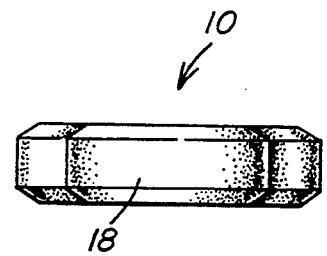
FIG. 2 is a side elevation of the tablet of FIG. 1.
Figure 3:
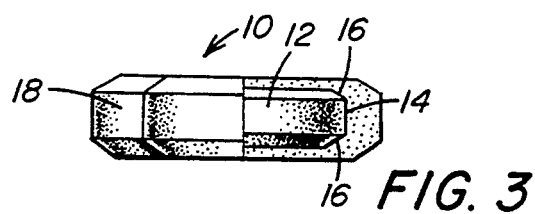
FIG. 3 is a side elevation similar to FIG. 2 with portion of the outer unit of the tablet broken away.

Referring to the drawings, and particularly to FIGS. 1 through 5, inclusive, there is shown a medicinal tablet 10 having a solid core unit 12 which has a cylindrical surface 14. Beveled edges 16 on the core unit provide a transition between the flat end surfaces of the core unit 12 and the cylindrical outer surface 14.

Figure 5:
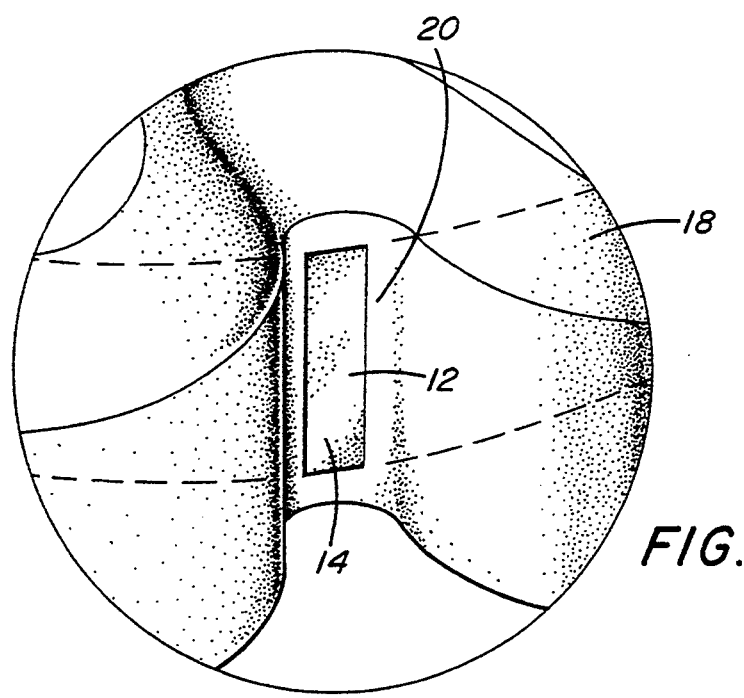
FIG. 5 is an enlarged view of the portion of the tablet of FIG. 1 showing the core unit exposed through the outer unit.

Formed around the core unit 12 is an outer unit 18 that is generally clover leaf in shape with three leaves. The indentations 20 between the leaves of the clover leaf shape each provide access to the cylindrical surface 14 on core unit 12 as is best seen in FIG. 5.

Figure 6:
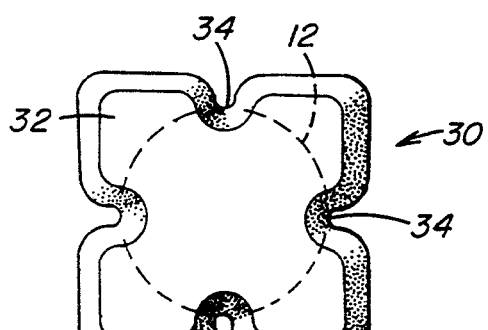
FIG. 6 is a top plan view of another form of the medicinal tablet of the present invention.
Figure 4:
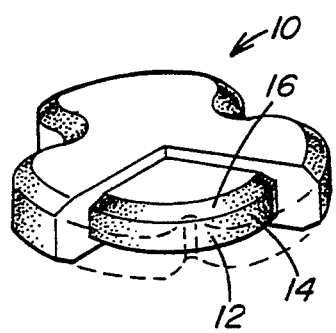
FIG. 4 is a perspective view of the tablet of FIG. 1 with a portion of the outer unit broken away.

FIG. 6 shows a medicinal tablet 30 having an outer unit 32. The outer unit of tablet 30 is generally square in shape and has indentations 34 formed therein. The core unit 12 in medicinal tablet 30 is identical to that described in connection with FIGS. 1 through 5, inclusive.

The solid core unit 12 contains a medically beneficial drug to be administered to a warm blooded animal with the tablet 10 or tablet 30 of the present invention. The outer unit 18 and the outer unit 32, respectively, are each formed of a polymeric composition that is inert and maintains its physical and chemical integrity during the lifetime of core unit 12. The phrase "physical and chemical integrity" indicates that the outer units 18 and 32, respectively, will not lose their structure and will not change during the dispensing life of the drug contained in core unit 12. Materials from which outer units 18 and 32 may be formed are cellulose acetate, cellulose diacetate or cellulose triacetate. Other polymeric compositions may be utilized for this purpose and the precise polymeric composition forms no part of the present invention. It is well known in the art to utilize polymeric compositions which maintain their physical and chemical integrity while a dosage unit contained within them is absorbed through the gastro-intestinal tract of warm blooded animals.

The core unit 12 of the present invention may also contain, in addition to the medically beneficial drug, a hydrogel form of a hydrophilic polymer that interacts with water and biological fluids and swells or expands. The hydrogel thereby forces the beneficial drug of the core unit 12 through the areas formed by indentations 20 or 34, respectively, in the tablets of the present invention so that the beneficial drug escapes the outer units 18 or 32, respectively. The hydrogel compositions form no part of the present invention and are well known in the art.

The core unit 12 is preferably a different, distinguishable color from the outer unit 18 and from the outer unit 32, respectively, of the tablets 10 and 30. When the distinguishable colors are utilized, the openings at indentations 20 and 34 permit the core unit 12 to be visualized. Such visualization provides quality control in that it may be ascertained that the proper core unit has been included in the medicinal tablet 10 or 30.

FIG. 7 illustrate a perspective view of a die 36 with a lower punch 38 and an upper punch 40 that may be utilized in a tablet making machine that is prevalent in the pharmaceutical industry. An example of such a tablet making machine is disclosed in U.S. Pat. No. 3,158,109 issued to F. T. Stott on Nov. 24, 1964, entitled "Multi-layer Tablet Making Machines".

The die 36 and punches 38 and 40 of FIG. 7 are of a size and shape to form the medicinal tablet 10 of FIGS. 1 through 5, inclusive. When utilized in a tablet making machine, the lower punch 38 is inserted into die 36 to a predetermined position. Powder from which the outer unit 18 is to be formed is then placed within die 36 in sufficient quantities to form the lower surface of tablet 10. The core unit 12 is then inserted into the die in the position shown in FIG. 7. Core unit 12 is located laterally by the shape of the indentations on the die 36 and the indentations on the die 36 contact the outer cylindrical surface of core unit 12 at three positions.

After core unit 12 is positioned on top of the powder that has been placed in die 36, an additional amount of the powder utilized to form outer unit 18 is added to the die 36 to surround the core unit 12 and to provide the thickness of the upper surface of tablet 10. Thereafter, the upper punch 40 is inserted into die 36 and a compressive force is exerted on die 36 and punches 38 and 40 to form the tablet as described in aforementioned U.S. Pat. No. 3,158,190. A modification to the standard tablet making machine must be made to insure that the core unit 12 arrives at the die in a flat position so that it is properly oriented laterally by the indentations in the die 36.

The amount of surface area of the core unit 12 that is exposed through outer unit 18 will control the speed with which the medically beneficial drug of core unit 12 is absorbed through the gastro-intestinal tract of an animal. One way of controlling the amount of surface area of core unit 12 that is exposed without changing the size of die 36 and punches 38 and 40 is to vary the height of the cylindrical surface 14 on core unit 12. FIGS. 8 and 9 illustrate how the surface area exposed may be so controlled.

In FIG. 8, core unit 12 has beveled edges 16 which result in a cylindrical height A to the surface 14. In FIG. 9, the bevelled edges 16' are substantially increased in size over the edges 16 shown in FIG. 8. The cylindrical surface 14' is, accordingly, reduced substantially to height B. Thus, the core unit 12 of FIG. 9 will have substantially less surface area exposed through outer unit 18 than does the core unit FIG. 8.

Utilizing the square tablet 30 of FIG. 6, an increased exposure of core unit 12 through outer unit 32 may be provided when the core unit 12 of FIG. 6 is identical to the core unit 12 of FIG. 1. As can be seen from FIGS. 1 and 6, FIG. 1 provides three indentations 20 while FIG. 6 provides four indentations 34. The square tablet 30 may be formed in the same type of tablet making machine as the cloverleaf table 10 when an appropriate die and die punches are provided.

It should be appreciated that in a widely utilized tablet making machine, a novel tablet that provides limited exposure to a medically beneficial drug within a solid core unit can be readily manufactured. The mechanical shape of the tablet controls the degree to which the medically beneficial drug is prolonged in its absorption through the gastro-intestinal tract of a warm blooded animal.

According to the provisions of the Patent Statutes, I have explained the principle, preferred construction and mode of operation of my invention and have illustrated and described what I now consider to represent its best embodiment. However, it should be understood that, within the scope of the appended claims, the invention may be practiced otherwise than as specifically illustrated and described.

I claim:

1. A mechanical configuration for a medicinal tablet comprising:

a solid core unit in the shape of a flat cylindrical tablet formed from a medically beneficial, biocompatible, non-toxic, drug;

an outer unit, surrounding said core unit, said outer unit being formed of a biocompatible, non-toxic polymer composition insoluble in the gastro-intestinal tract of warm blooded animals while said core unit is being absorbed through said gastro-intestinal tract;

said outer unit being of a shape that said outer unit exposes a portion of the outer cylindrical surface area said core unit therethrough when said outer unit is formed around said core unit.

2. The method of forming in a die the mechanical configuration for a medicinal tablet having a solid core unit formed from a medically beneficial, biocompatible, non-toxic drug surrounded by an outer unit formed of a biocompatible, non-toxic polymer composition powder wherein a portion of the surface area of said core unit is exposed through said outer unit, said method comprising the steps of:

a. obtaining a solid core unit having the desired medically beneficial, biocompatible, non-toxic drug and shaped as a generally cylindrical flat tablet;

b. inserting into a die having the peripheral shape of said outer unit a first quantity of powder from which said outer unit is formed;

c. inserting into said die said solid core unit so that portions of said core unit cylindrical surface abut said die and said die locates said core unit at a fixed lateral position within said die;

d. inserting into said die over said core unit a second quantity of powder from which said outer unit is formed;

e. inserting a mating die punch into said die;

f. exerting compressive force within said die by said mating die punch to force said first and second quantities of powder into the shape of said outer unit whereby said core unit outer cylindrical surface is exposed through said outer unit at those places on said core unit outer cylindrical surface that abut said die; and g. thereafter removing said mechanical configuration for a medicinal tablet from said die.

3. The method of claim 2 wherein said die peripheral shape forms a generally coverleaf shape mechanical configuration for a medicinal tablet having three leaves.

4. The method of claim 2 wherein said die peripheral shape forms a generally square shaped mechanical configuration for a medicinal tablet.

5. The mechanical configuration for a medicinal tablet of claim 1 wherein said outer unit maintains its physical and chemical integrity during the dosage life of said solid core unit.

6. The mechanical configuration for a medicinal tablet of claim 1 wherein said solid core unit includes a hydrophilic hydrogel that expands upon contact with fluids in the gastro-intestinal tract of warm blooded animals to help force said medically beneficial, biocompatible, non-toxic drug of said core unit through the areas of said outer unit that expose said core unit.

7. The mechanical configuration for a medicinal tablet of claim 1 wherein said outer unit is formed in the general shape of a cloverleaf having three leaves that exposes three separate outer cylindrical surface areas of said core unit therethrough.

8. The mechanical configuration for a medicinal tablet of claim 1 wherein said outer unit is formed in the general shape of a square that exposes four separate outer cylindrical surface areas of said core unit therethrough.

9. The mechanical configuration for a medicinal tablet of claim 1 wherein the portion of outer cylindrical surface area of said core unit exposed can be varied by varying the height of the cylindrical surface of said core unit.

10. A mechanical configuration for an oral medicinal tablet comprising;

a solid core unit formed from a medically beneficial, biocompatible, non-toxic drug, said core unit being a flat, generally cylindrically shaped tablet with beveled top and bottom edges;

an outer unit, surrounding said core unit, the shape of said outer unit causing a portion of the cylindrical outer surface of said core unit between said beveled top and bottom edges to be exposed through said outer unit;

said outer unit being formed of a biocompatible, non-toxic polymer material that is insoluble in the gastrointestinal tract of warm blooded animals whereby said outer unit maintains its physical and chemical integrity throughout the dosage life of said core unit while said core unit medically beneficial drug is absorbed through the gastro-intestinal tract.

11. The mechanical configuration for a medicinal tablet of claim 10 wherein said solid core unit includes a hydrophilic hydrogel that expands upon contact with fluids in the gastro-intestinal tract of warm blooded animals to help force said medically beneficial, biocompatible, non-toxic drug of said core unit through the areas of said outer unit that expose said core unit.

12. The mechanical configuration for a medicinal tablet of claim 10 wherein said outer unit is formed in the general shape of a cloverleaf having three leaves that exposes three separate outer cylindrical surface areas of said core unit therethrough.

13. The mechanical configuration for a medicinal tablet of claim 10 wherein said outer unit is formed in the general shape of a square that exposes four separate outer cylindrical surface areas of said core unit therethrough.

14. The mechanical configuration for a medicinal tablet of claim 10 wherein the portion of outer cylindrical surface area of said core unit exposed can be varied by varying the height of the cylindrical surface of said solid core which, can, in turn, be varied by increasing or decreasing the size of the bevel on said beveled edges.

15. The mechanical configuration for a medicinal tablet of claim 10 wherein said core unit is a distinguishable different color from said outer unit.

16. The method of claim 2 wherein the amount of said portion of surface area of said core unit that is exposed through said outer unit can be varied by varying the height of the cylindrical surface of said solid core unit without changing said die or said die punch.

* * * * *